(12) United States Patent
Villanti et al.

(10) Patent No.: US 6,239,312 B1
(45) Date of Patent: May 29, 2001

(54) METHOD FOR THE PREPARATION OF SALTS OF CARBOXYLIC ACIDS USING COPPER CATALYZED DEHYDROGENATION

(75) Inventors: Alberto Villanti, Milan; Gianna Conti, Brescia, both of (IT)

(73) Assignee: Finichimicia S.p.A., Manerbio (IT)

( * ) Notice: Subject to any disclaimer, the term of this patent is extended or adjusted under 35 U.S.C. 154(b) by 0 days.

(21) Appl. No.: 09/271,135

(22) Filed: Mar. 17, 1999

(30) Foreign Application Priority Data

Mar. 23, 1998 (IT) ................................ TO98A0249

(51) Int. Cl.⁷ .................................... C07C 51/16
(52) U.S. Cl. .................... 562/526; 562/539; 562/553; 562/571; 562/572
(58) Field of Search .................... 562/526, 553, 562/571, 572, 539

(56) References Cited

U.S. PATENT DOCUMENTS

| 4,782,183 | | 11/1988 | Goto et al. . |
| 5,220,054 | * | 6/1993 | Urano et al. . |
| 5,225,592 | | 7/1993 | Ochoa et al. . |
| 5,292,936 | | 3/1994 | Franczyk . |
| 5,367,112 | | 11/1994 | Franczyk . |
| 5,627,125 | * | 5/1997 | Ebner et al. . |
| 5,689,000 | * | 11/1997 | Enber et al. . |
| 5,916,840 | * | 6/1999 | Ebner et al. . |
| 5,986,128 | * | 11/1999 | Smith . |

FOREIGN PATENT DOCUMENTS

| 0 506 973 | 10/1991 | (EP) . |
| 0 504 381 | 9/1992 | (EP) . |
| WO 92/06069 | 4/1962 | (WO) . |

* cited by examiner

*Primary Examiner*—Gary Geist
*Assistant Examiner*—Robert W. Deemie
(74) *Attorney, Agent, or Firm*—Kramer, Levin, Naftalis, & Frankel LLP.

(57) ABSTRACT

A method for the production of a salt of carboxylic acid by catalytic dehydrogenation effected by reacting the corresponding primary alcohol in aqueous solution with an alkaline hydroxide in the present of a copper catalyst, in which, before the catalytic dehydrogenation, the mass of the reagents comprising the said aqueous solution of a primary alcohol is subjected to a deoxygenation stage in order to remove or reduce the level of dissolved molecular oxygen. The deoxygenation stage is preferably carried out by bubbling an inert gas or by adding a reducing agent.

9 Claims, No Drawings

METHOD FOR THE PREPARATION OF SALTS OF CARBOXYLIC ACIDS USING COPPER CATALYZED DEHYDROGENATION

The present invention relates to a method for the preparation of salts of carboxylic acids and, particularly, salts of aminocarboxylic acids, by means of catalytic dehydrogenation effected by reacting the corresponding primary alcohol with an alkaline metal hydroxide in the presence of a copper catalyst.

The salts of the carboxylic acids have numerous applications in many fields; many salts, transformed into the corresponding acids, are used as primary materials in the preparation of pharmaceutical products, agrochemical products and pesticides.

The salts of aminocarboxylic acids, such as glycine salts, iminodiacetic acid salts and nitriltriacetic acid salts, are of particular interest.

U.S. Pat. No. 4,782,183 in the name Goto et al describes a method for preparing salts of aminocarboxylic acids in which the corresponding amino alcohol is subjected to the action of alkaline metal hydroxides in the presence of a Raney copper catalyst.

Although the use of Raney copper as a catalyst has substantial economic advantages in comparison with the use of noble metal catalysts, an inherent problem with its use lies in the fact that it rapidly becomes poisoned; it has, in fact, been observed that the activity of the copper-based catalyst decreases with repeated use, rapidly increasing costs to economically unacceptable levels.

International patent application no. WO92/06069 describes a method for the production of salts of glycine, iminodiacetic acid and nitriltriacetic acid in which monoethanolamine, diethanolamine or triethanolamine are brought into contact with an alkaline metal hydroxide in the presence of a Raney copper catalyst, and in which the catalyst is regenerated after each use by treatment with formic acid.

U.S. Pat. Nos. 5,292,936 and 5,367,112, both in the name of Franczyk, describe a method for catalytic dehydrogenation using a Raney copper catalyst treated in an addition reaction using particular metals, such as chrome, titanium and molybdenum; in this way, it is possible to prolong significantly the life of the catalyst, thus making its use in the industrial production of salts of carboxylic acids economically advantageous.

Other known processes utilise Raney copper as a catalyst in oxidative processes. In particular, U.S. Pat. No. 5,225,592 describes a method for the production of salts of amino carboxylic acids by means of the oxidation of the corresponding alcohol in the presence of alkaline hydroxide and Raney copper with molecular oxygen, or a gas containing molecular oxygen, in which the oxygen partial pressure in the reactor is maintained between approximately 2 to 20 kg/cm$^2$.

Similarly, EP-B-0 506 973 describes a method for the production of salts of aminocarboxylic acids by means of the oxidative dehydrogenation of the amino alcohol with a copper catalyst with the addition to the reaction medium of aluminium or an aluminium-containing compound.

An object of the present invention is to provide a method that is simple from the operative point of view, and particularly advantageous from the economical point of view, which prolongs the life of the catalyst, maintaining the high activity thereof even after several tens of recyclings.

Another object of the invention is to provide a method which enables the economical use of a commercial Raney copper catalyst, which enables the advantageous conversion of amino alcohols of industrial interest into the corresponding carboxylic acids in salt form.

The invention provides a method for the production of a salt of carboxylic acid by catalytic dehydrogenation effected by reacting the corresponding primary alcohol in aqueous solution with an alkaline hydroxide in the presence of a copper catalyst, characterised in that, before the catalytic dehydrogenation, the reaction mass comprising the said aqueous primary alcohol solution is subjected to a deoxygenation stage for the removal or reduction of the level of dissolved molecular oxygen.

The primary alcohols that can be used as starting products in the process of the present invention can be aliphatic, cyclic or aromatic alcohols, and are those that are known to the experts in the field. The only requirement that the alcohol and the corresponding carboxylic acid must satisfy is for both to be stable under the severe conditions in which the process of the invention is conducted.

In particular, the method is applicable to primary amino alcohols, represented by the formula (1):

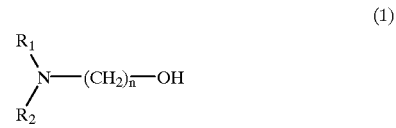

(1)

in which:

n is between 2 and 10, and

R$_1$ and R$_2$, independently of each other, are preferably chosen from the group comprising hydrogen, —CH$_2$—CH$_2$OH, —CH$_2$—COOH, alkyls having from 1 to 6 carbon atoms and phosphonomethyl.

If R$_1$ is hydrogen and R$_2$ is —CH$_2$—CH$_2$OH, the product resulting from the conversion of the amino alcohol is the salt of iminodiacetic acid.

Typically, the process is carried out by introducing an aqueous solution of the primary alcohol, an alkaline hydroxide and the appropriate quantity of Raney copper catalyst into a nickel autoclave.

The autoclave, which has a controllable discharge valve, is taken to the predetermined temperature, generally between 100° and 220° C., at which the alcohol is converted to the salt of the corresponding carboxylic acid according to the reaction (2) which, by way of example, refers to the conversion of diethanolamine:

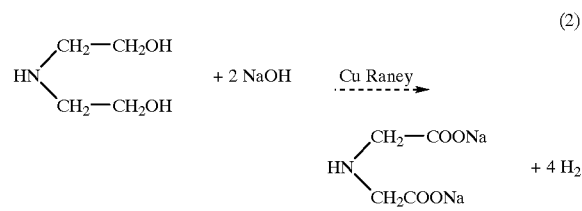

(2)

After sufficient time to enable the completion of the reaction, the reaction mass is filtered to recover the catalyst which is then recycled in a subsequent reaction.

As is illustrated in the following comparative example 1, in the absence of special precautions, the activity of the Raney copper decreases fairly rapidly and, within six or seven recyclings, in substantially the same time, the yield falls from 98% to approximately 67%.

According to the invention, it has been found that by eliminating or strongly reducing the presence of the dissolved oxygen in the reagents, the activity of the catalyst decreases surprisingly more slowly, so that the same catalyst can be reused many tens of times with a limited loss of activity.

The elimination of the oxygen, or its substantial reduction, can be achieved using physical or chemical means.

The physical elimination is effected by means of stripping, for example, by bubbling an inert gas or water vapour, preferably helium or nitrogen, through the aqueous solution of the primary alcohol. This operation is preferably carried out immediately before loading the solution in the autoclave which is then preferably, immediately, cleansed with repeated vacuum/nitrogen cycles.

The bubbling time of the inert gas and the insufflation capacity necessary to reduce the level of dissolved oxygen to levels that will prolong the life of the catalyst depend on the efficiency of the bubbling system used, and can be determined by a technical expert in the field by prior testing.

A level of dissolved oxygen less than 0.2–0.3 ppm is particularly preferred.

The chemical removal is effected by means of the addition of appropriate quantities of reducing substances to the aqueous solution of the primary alcohols. The aforesaid reducing substances can be organic or inorganic, although they must be soluble in the reaction mass and such that they do not interfere with the progress of the reaction.

By way of non-limitative. example, reducing substances such as sodium formate can advantageously be used.

The quantity of reducing agent added to the reaction mass is preferably between 0.1 and 0.5% by weight, with reference to the total reaction mass.

The quantity of catalyst used to convert the alcohol can vary from 1 to 70% by weight with respect to the alcohol, and preferably from 10 to 40% by weight. These percentages are calculated with respect to the dry content of Raney copper in its aqueous formulation.

The alkaline metallic hydroxides used in the method are those known to the experts in the field. The quantity of hydroxide is at least equal to one equivalent per equivalent of hydroxyl groups present in the alcohol utilised in the reaction. Sodium hydroxide and potassium hydroxide are preferred because of their availability and economy.

The temperature at which the process is conducted is preferably between 150° and 200° C.; the pressure is generally between 5 and 50 kg/cm$^2$, and preferably between 8 and 12 kg/cm$^2$.

The pressure control valve is set depending on the vapour pressure of the water at the predetermined reaction temperature in order to enable the hydrogen that forms during the reaction to be easily discharged.

The invention will now be described in greater detail in the following examples, given purely by way of non-limitative example.

EXAMPLE 1 (comparative)

This example illustrates the performance of the catalyst used without special precautions for protecting its activity. 40 g of diethanolamine (0.38 moles), 85 g of water, 32 g of NaOH in drops (0.80 moles) and 16 g of commercially-available Raney cooper containing 50% of water were introduced into a 500 ml nickel autoclave provided with a magnetically driven mechanical stirrer. The autoclave was closed, cleansed three times with a vacuum/nitrogen, kept under agitation and heated to a temperature of 170° C. The pressure was allowed to rise and was held at 9 kg/cm$^2$, by adjusting the appropriate discharge valve of the autoclave.

Except for the first two cycles, the reaction was interrupted after a fixed time period of 4.5 hours and the mass analysed to determine the yield of disodium imminodiacetate. The catalyst, separated by filtration from the reaction mass, was reused in a subsequent reaction. Table 1shows the results of the tests.

TABLE 1

Yield using unprotected catalyst

| Cycle No. | Reaction Time (h) | % Molar Yield |
|---|---|---|
| 1 | 2.7 | 98.0 |
| 2 | 3.5 | 90.0 |
| 3 | 4.5 | 85.3 |
| 4 | 4.5 | 78.2 |
| 5 | 4.5 | 71.4 |
| 6 | 4.5 | 69.0 |
| 7 | 4.5 | 66.9 |

EXAMPLE 2

The example illustrates the use of the catalyst in the case of reduction of the presence of oxygen by physical means (degassing).

125 g of an aqueous solution of diethanolamine containing 40 g of diethanolamine (0.38 moles) were added to a 500 ml nickel autoclave provided with a magnetically driven mechanical stirrer. This solution was prepared by weighing the appropriate quantity of the two components of the solution into a flat-bottomed conical flask and then bubbling the solution with helium using a diffuser for five minutes. Then, 32 g of NaOH in drops (0.8 moles) and 16 g of commercially-available Raney copper containing 50% of water were added to the autoclave. The autoclave was closed, cleansed rapidly three times using a vacuum/nitrogen, kept under agitation and heated to 170° C.

The pressure was allowed to rise and was held at 9 kg/cm$^2$, by controlling the appropriate discharge valve of the autoclave. When the production of hydrogen stopped, the reaction was stopped and the mass was analysed to determine the yield of disodium imminodiacetate. The catalyst, separated by filtration from the reaction mass, was kept in water degassed using helium awaiting its reutilisation in a subsequent reaction.

Table 2 shows the results of the tests.

TABLE 2

Reaction with degassed reagents

| Cycle No. | Reaction Time (h) | Yield (Molar %) |
|---|---|---|
| 1 | 2.7 | 98.0 |
| 2 | 3.0 | 98.2 |
| 3 | 3.5 | 98.1 |
| 4 | 3.8 | 98.2 |
| 5 | 4.0 | 98.0 |
| 10 | 4.9 | 97.9 |
| 15 | 6.0 | 97.7 |
| 20 | 6.6 | 97.4 |
| 25 | 7.5 | 97.5 |
| 30 | 8.4 | 97.6 |

EXAMPLE 3

The example illustrates the use of the catalyst in the case of reduction of the presence of oxygen by chemical means, by adding sodium formate.

The procedure described in example 2 was followed except for the fact that instead of degassing the reagents using helium, 0.3 g sodium formate was added to the reaction mass for each cycle.

Table 3 shows the results of the tests.

TABLE 3

| Cycle No. | Reaction Time (h) | Yield (Molar %) |
|---|---|---|
| 1 | 2.7 | 98.0 |
| 2 | 3.0 | 98.3 |
| 3 | 3.5 | 97.9 |
| 4 | 3.8 | 98.1 |
| 5 | 4.0 | 98.0 |
| 10 | 4.5 | 97.5 |
| 15 | 4.8 | 97.5 |
| 20 | 5.0 | 97.3 |
| 25 | 5.8 | 97.2 |
| 30 | 6.5 | 97.4 |

What is claimed is:

1. A method for the production of a salt of carboxylic acid by catalytic dehydrogenation comprising reacting a corresponding primary alcohol in aqueous solution with an alkaline hydroxide in the presence of a copper catalyst, wherein, before the catalytic dehydrogenation, the mass of reagents comprising the said aqueous solution of primary alcohol is subjected to a deoxygenation stage to remove or reduce the level of dissolved molecular oxygen.

2. The method according to claim 1, wherein the said deoxygenation stage comprises bubbling an inert gas or water vapour.

3. The method according to claim 2, wherein the inert gas is helium or nitrogen.

4. The method according to claim 1, wherein the deoxygenation stage comprises adding a reducing agent to the mass of reagents.

5. The method according to claim 4, wherein the reducing agent is sodium formate.

6. The method according to claim 1, wherein the said primary alcohol is a compound of the formula:

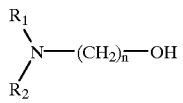

wherein n is an integer between 2 and 10, and wherein $R_1$ and $R_2$ are chosen independently of each other and are selected from the group consisting of: hydrogen, —$CH_2CH_2OH$, $CH_2OOH$, alkyls having from 1 to 6 carbon atoms and phosphomethyl.

7. The method according to claim 1, wherein the catalytic dehydrogenation is carried out at a pressure of between about 5 and about 20 $kg/cm^2$, and at a temperature of between about 100° C. and about 200° C.

8. The method according to claim 1, wherein the alkaline hydroxide is selected from the group consisting of sodium hydroxide and potassium hydroxide, the said alkaline hydroxide being utilised in a quantity equal to at least one equivalent per equivalent hydroxyl group present in the primary alcohol.

9. The method according to claim 1, wherein the catalyst comprises Raney copper, and wherein the Raney copper comprises from about 10 to about 40% by weight with respect to the alcohol, the said percentage being calculated with respect to the dry content of the Raney copper.

* * * * *

UNITED STATES PATENT AND TRADEMARK OFFICE
CERTIFICATE OF CORRECTION

PATENT NO.     : 6,239,312 B1
DATED          : May 29, 2001
INVENTOR(S)    : Villanti et al.

It is certified that error appears in the above-identified patent and that said Letters Patent is hereby corrected as shown below:

<u>Title page,</u>
Item [73], the Assignee "Finichimicia S.p.A" should read -- Finchimica S.p.A. --

Signed and Sealed this

Twenty-third Day of July, 2002

*Attest:*

JAMES E. ROGAN
*Attesting Officer*     *Director of the United States Patent and Trademark Office*